United States Patent [19]

Bolz et al.

[11] 4,020,151

[45] Apr. 26, 1977

[54] METHOD FOR QUANTITATION OF ANTIGENS OR ANTIBODIES ON A SOLID SURFACE

[75] Inventors: Gunner Bolz, Santa Clara; Fred H. Deindoerfer, Northridge; Chun P. Hu, Santa Clara; Naomi Kameda, Foster City; Robert Wang, San Jose, all of Calif.

[73] Assignee: International Diagnostic Technology, Inc., Santa Clara, Calif.

[22] Filed: Feb. 17, 1976

[21] Appl. No.: 658,298

[52] U.S. Cl. .............................. 424/1.5; 23/230 B; 424/12
[51] Int. Cl.² ................ G01N 33/00; G01N 33/16; G21H 5/02
[58] Field of Search .......... 23/230 B, 230.6; 424/1, 424/1.5, 12

[56] References Cited

UNITED STATES PATENTS

| | | | |
|---|---|---|---|
| 3,551,555 | 12/1970 | Schuurs | 424/12 |
| 3,555,143 | 1/1971 | Axen et al. | 424/1.5 |
| 3,646,346 | 2/1972 | Catt | 424/12 |
| 3,790,663 | 2/1974 | Garrison et al. | 424/12 |

OTHER PUBLICATIONS

Catt et al., J. of Lab. & Clin. Med., vol. 70, p. 820, 1967.
Wide, Acta Endocrinologia Supplementum, vol. 63, No. 142, pp. 207-221.

*Primary Examiner*—Benjamin R. Padgett
*Assistant Examiner*—Christine M. Nucker
*Attorney, Agent, or Firm*—Flehr, Hohbach, Test, Albritton & Herbert

[57] ABSTRACT

A method for quantitation of antigens or antibodies from a liquid sample on a solid surface. The sample is first sorbed directly to a nonimmunological surface. Then the surface is exposed to antibody or antigen labelled preferably with a fluorogen, to cause an immunological reaction to occur. After removal of unreacted reagent from the surface, the quantity of reacted labelled reagent is determined, as for example, fluorogen by a fluorometer. When the sample includes significant quantities of protein other than the antigen or antibody to be quantitated, buffer protein unreactive with the labelled antigen or antibody is added in concentrations sufficient to minimize the dependence of sorbed antigen or antibody upon variations in the concentration of such other protein.

10 Claims, No Drawings

METHOD FOR QUANTITATION OF ANTIGENS OR ANTIBODIES ON A SOLID SURFACE

BACKGROUND OF THE INVENTION

Solid-phase radioimmunoassay (RIA) of antigens or antibodies in a serum sample are well known. Catt and his co-workers have reported such techniques on the surface of plastic tubes (Science, 158: 1570 (1967); U.S. Pat. No. 3,646,346) and plastic discs (J. Lab. & Clin. Med., 70: 820 (1967). In such techniques, an excess of specific antibody is first adsorbed to a support surface. Then, the sample to be assayed is immunologically reacted with such surface in a sandwich or competitive binding technique. In the competitive binding technique, illustrated in U.S. Pat. No. 3,555,143, the concentration of antigen to be determined and a known quantity of radioactively tagged antigen are immunologically reacted with the antibodyadsorbed surface. The labelled antigen bound to the antibody on the surface is then quantitated to determine indirectly the total quantity of antigen in the original sample. It is known that such a competitive binding technique is relatively inaccurate, especially when the proportions of labeled and unlabelled antigen are diverse. In the sandwich technique, serum containing an unknown concentration of antigen is immunologically reacted with the antibody-containing surface. Then in a following step, the bound antigen is incubated with labelled antibody and the amount of immunologically bound, labelled antibody is subsequently measured. This technique includes the disadvantage of adding an additional step to the procedure.

One common disadvantage to both of the foregoing techniques is apparent when support surfaces therein used are mass produced for distribution to clinical laboratories for testing of serum or the like. An antibody specific for each antigen must be predeposited in order for the antigen concentration to be determined in the laboratory of the customer. The only alternative for the customer is to perform the preliminary antibody coating step which can be time consuming and subject to error. Another problem with shipping of such antibody coated surfaces is that they are composed of protein, which is biologically active and so susceptible to deterioration or denaturation in the presence of light, heat, alterations of pH levels, enzymes, bacteria, or other environmental conditions. This problem was recognized in U.S. Pat. No. 3,790,663 which discloses a specific preparation of a dry antiserum coated solid-phase for RIA of antigens to increase the stability of the antiserum. It is apparent that even such dry surfaces are less stable than the underlying polymeric substrate and, additionally, would require special handling to prevent removal of the antiserum as from the environment or by physical abrasion.

SUMMARY OF THE INVENTION AND OBJECTS

In accordance with the present invention, a method is provided for quantitating antigen or antibody in a liquid sample performed on a solid surface. For simplicity of description, the material guantitated is assumed to be an immunoglobulin antigen in a sample of blood serum. The sample is sorbed directly onto an immunologically unreactive solid support surface such as a polyacrylic polymer adsorptive for the immunoglobulin. (Alternatively, such sorption may be by ionic binding as to ion exchange resin.) The immunoglobulin would be adsorbed onto the surface in proportion to its concentration in the serum. After adsorption, the surface is exposed to an aqueous reagent including an excess of labelled antibody specific to the immunoglobulin to cause an immunological reaction. Then, after removal of unreacted labelled antibody from the surface, the quantity of reacted labelled antibody is measured. If the substance in the sample is to be detected as an antibody rather than as an antigen, labelled specific antigen immunologically reactive with the sample antibody is reacted with the surface.

When the sample is of a type, e.g., serum, which includes a significant quantity of proteins other than the antigen or antibody to be quantitated, excess buffer protein unreactive with the labelled antigen or antibody is added to the sample to minimize the dependence of adsorbed antibody or antigen to be quantitated upon variations in the concentration of such other protein in the sample.

It is an object of the invention to provide a rapid, accurate method for the quantitation of antigen or antibody on a solid surface which overcomes the aforementioned disadvantages of the prior art techniques.

It is another object of the invention to provide a method of the foregoing type which eliminates the necessity for first coating the surface with an antigen or antibody.

It is a specific object to permit rapid quantitative determinations of human immunoglobulin concentrations in blood serum.

Further objects and features of the invention will be apparent from the following description of its preferred embodiments.

DETAILED DESCRIPTION OF THE PREFERRED EMBODIMENTS

The present invention relates to a method for the quantitation on a solid support surface of antigen or antibody contained in a liquid sample. If the sample material to be quantitated is an antigen, it is immunologically reacted with a labelled specific antibody which is subsequently detected. Conversely, if the material in the sample to be quantitated is an antibody, it can also be immunologically reacted with labelled specific antigen for subsequent detection and measurement. For simplicity of description, the liquid sample described herein comprises blood serum. Also, the substance to be quantitated in the blood serum will be referred to as antigen.

Briefly summarized, the preferred embodiment of the invention comprises the following sequence of steps. Serum antigen is adsorbed directly onto the solid support surface. After removal of of unadsorbed sample, the surface is exposed to reagent containing labelled specific antibody immunologically reactive with the sample antigen to cause the immunological reaction to occur. Thereafter, unreacted labelled antibody is removed and the quantity of reacted labelled antibody is measured. Prior to the adsorption step, a predetermined quantity of buffer protein unreactive with labelled antibody is added to the sample to minimize the dependence of antigen to be quantitated on the variations in concentration of other protein in the sample.

In a typical instance, a serum sample is obtained by collecting blood without anticoagulant by conventional procedures and allowing the blood to clot.

In the first step of the present procedure, the protein of the blood serum is sorbed, preferably by physical adsorption, to an immunologically unreacted solid support surface adsorptive for the anrigen. This distinguishes from the foregoing prior art systems in which a layer of antibody specifically reactive with the antigen to be detected is first deposited on the surface prior to contact with the sample to be assayed. A suitable technique of adsorption is immersion of the support surface in a test tube of serum sample, and mixing the same thoroughly, as with an automatic shaker, for approximately 20 minutes.

A suitable solid support surface is formed of a water-insoluble polymeric material sorptive for the antigen. Known materials of this type include hydrocarbon polymer such as polystyrene, polyethylene, polypropylene, polybutylene, butyl rubber and other synthetic rubbers. Other suitable organic polymers include silastic rubber, polyesters, polyamides, cellulose and cellulosic derivatives, acrylates, methacrylates, and vinyl polymers such as vinyl chloride, and polyvinyl fluoride. Copolymers such as graft copolymers of polystyrene are also useful. In addition to the foregoing materials, the solid support surface may comprise silica gel, silicone wafers, glass, insoluble protein, and metallic surfaces (e.g., tantalum coated glass).

A particularly effective form for the solid support surface is a disc, such as formed of polymethylmethacrylate film. After completion of the reactions described hereinafter, the technique of reading the labelled substance on the support surface may follow the detection technique set forth in application Ser. No. 627,941, filed Nov. 3, 1975, entitled "Diagnostic Reagent Holder and Method".

In a blood serum sample, the total protein content may vary, say, from 3 to 12%. The basis of the quantitation of the immunoglobulin to be detected is that the amount of immunoglobulin adsorbed onto the surface is proportional to its concentration in the serum sample. This assumes that the concentrations of the other substances in the serum that adsorb onto the surface remain essentially constant and that the surface is relatively nonspecific with respect to the different adsorbed substances, predominantly proteins. Neither of these assumptions is totally accurate. (L. Vroman, et al, Advances in Chemistry Series, No. 45 (1976). However, variations in the above factor underlying these assumptions that may effect accurate quantitation may be minimized as follows.

It is apparent that the antigen to be quantitated competes with other protein in the serum for adsorption sites on the support surface. The term "other protein", as used herein, will refer to the protein content other than the original antigen or antibody to be measured in the liquid sample. Thus, variation in the quantity of such other protein correspondingly will vary the amount of adsorbed antigen resulting in errors in quantitation of antigen. It has been found that this cause of error can be reduced to a minimum by the addition to the serum sample prior to adsorption of a predetermined quantity of buffer protein unreactive with the labelled antibody at a concentration sufficient to minimize the dependence of adsorbed antigen upon the variable content of the other protein in the sample. The term "buffer protein" will refer to protein added to the original sample which is unreactive with the subsequently added labelled antigen or antibody and which minimizes the effect of variation in the final quantitation upon the variation of other protein. Preferably, the ratio of buffer protein to total protein in the serum or other protein is in excess of 1:1 by weight. The effect of buffer protein is illustrated by adding, say, a ten fold excess over other protein. In that instance, variation of other protein would not vary the adsorbed antigen to any significant extent.

The buffer protein solution comprises a stable adsorbable protein which is unreactive with the specific antibody for the antigen to be detected. A suitable solution for this purpose comprises a 0.125% by weight solution of bovine serum albumin in phosphate buffered saline at a pH of 7.5.

The foregoing Vroman publication reports that there is some variation in the adsorption affinity of various proteins for different polymeric surfaces or different types of samples were employed as a reference. Accordingly, calibration of a reference curve should utilize the same type of support surface and the same of sample, e.g., serum or equivalent, and the same buffer protein solution to minimize the effect upon quantitation of this variation in adsorption affinity.

After adsorption of serum antigen, the surface is washed with an appropriate solution to remove unadsorbed components of the serum sample. The aforementioned buffer protein solution is an example of such an appropriate solution. After washing, the support surface containing antigen is exposed to an excess of a labelled specific antibody immunologically reactive with the antigen to cause an immunological reaction to occur on the surface. The duration of the immunological reaction step should be sufficient for completion of the reaction. A suitable time for this purpose is on the order of 5 minutes to two hours during which the sample is constantly mixed as by shaking.

Any conventional labelling substance may be attached to the antibody to be reacted with the antigen on the surface. Such labelled substance may include a luminescent substance such as a phosphor or fluorogen, a radioactive substance, an enzyme, or a metal containing substance.

After completion of the immunological reaction, the support surface is washed in a buffer solution to remove unreacted labelled antibody from the surface which could interfere with the quantitation. An effective washing solution comprises phosphate buffer saline solution.

After washing, the surface is read in an appropriate reading device. The present system is particularly adapted for fluorescent detection of the surface of a diagnostic reagent holder of the type set forth in the aforementioned co-pending patent application. Thus, the holder containing the fluorescently labelled disc is placed into a viewing housing for reading by a fluorometer. Such readings can be taken in less than 10 seconds.

The aforementioned fluorometric readings are compared against known reference preparations adsorbed similarly upon identical surfaces. For example, for the specific immunoglobulin to be read, calibration curves are prepared for different concentrations of immunoglobulin versus the fluorescent signal in arbitrary units. As guidance, the assay ranges for routine methodology of serum samples are as follows: IgG — 300 to 2,000 mg/dl; IgA — 35 to 330 mg/dl; and IgM — 15 to 300 mg/dl.

Suitable fluorescent labels include lissaminerhodamine B, D.A.N.S. (1-dimethylamino-naphthalene-5-sulfonic acid), ortho-phthaladehyde, fluorescein isothiocyanate and fluorescamine, which are frequently used in fluorescence microscopy. The first two possess an orange or red emission spectra rather than the yellow green fluorescein and the second two possess a blue or green emission spectra. The only variation in the fluorometer would be in the change in excitation and emission filters used, as well as the changes in the fluorescent tag on the antibodies in the reagent kit.

When the label comprises a radioactive substance, a suitable reading device is a scintillation counter.

The present technique is also applicable to the use of enzyme labelled systems. One such system is described in an article by Pesce et al entitled "Use of Enzyme-Linked Antibodies to Measure Serum Anti-DNA Antibody in Systemic Lupus Erthyematosus", Clin. Chem. 20/3, 353-359 (1974). The described system differs from the one described herein in that the diagnostic reagent, DNA, is adsorbed to a test tube support. Thereafter, anti-DNA antibody containing serum is reacted with the coated tube followed by reaction with an anti-human gamma globulin peroxidase enzyme conjugate. Then a colored reaction product is developed by action of peroxidase on a substrate which is colorimetrically measured by conventional techniques.

The present solid surface technique is preferably performed with a fluorescently labelled antigen or antibody. An effective reagent is a fluorescein isothiocyanate labelled monospecific antibody to human IgG, IgA, or IgM in a buffered saline solution. Fluorescent labelling permits quantitation using a fluorometer reading a precise predetermined area comprising only the reaction support surface. This can be accomplished by viewing such surface through a window of a viewing housing framed by opaque material which permits detection of fluorescence emitted only from the surface. This would be difficult to accomplish with a radioactively labelled substance. A particularly effective viewing housing and reaction support surface is illustrated in the aforementioned patent application Ser. No. 627,941, incorporated herein by reference. The support surface comprises the disc attached to the diagnostic reagent holder of said application. The importance of viewing only the support surface is that there is a degree of carryover of labelled substance which attaches to the holder in addition to that which attaches to the disc. This is a particular problem in the present technique in which the sample protein may adsorb relatively nonspecifically in significant quantities to the holder as well as the disc, especially if the holder is formed of a polymer adsorptive for protein.

Although physical adsorption is preferred as the sorption technique employed herein because of its simplicity and the inexpensive nature of the support surface, it should be understood that other sorption techniques may be employed within the scope of the present invention. For example, specially treated ion exchange resins may be employed as the surface for ionic bonding of the antigen or antibody to be measured. This may be desirable for vitamin $B_{12}$ and other molecules that bind readily to ion exchange resins.

A further disclosure of the nature of the present invention is provided by the following specific examples of the practice of the invention. It should be understood that the data disclosed serve only as examples and are not intended to limit the scope of the invention.

EXAMPLE 1

In the determination of the concentration of human IgG, a serum sample is prediluted in a 1:10 ratio by volume with protein buffer solution at a 0.125% concentration of bovine serum albumin in phosphate buffered saline at pH 7.7 ± 0.1 including a 0.1% sodium azide preservative. 5 microliters of this diluted sample is pipetted into a test tube containing 500 microliters of the above buffer and thoroughly mixed. Then a solid support surface comprising a polymethylmethacrylate polymer disc attached to a holder is immersed into the tube and shaken for 20 minutes to permit sufficient adsorption to occur for subsequent analysis. Thereafter, the disc is transferred to another test tube containing the same protein buffer solution and shaken for 5 minutes to wash unadsorbed antigen from the surface.

Thereafter, the support surfaces are immersed in an excess of labelled antibody comprising appropriate monospecific fluorescein isothiocyanate labelled goat antibody to human IgG, diluted appropriately in phosphate buffered saline at pH 7.5 ± 0.5 containing 0.125% BSA.

The support surface is thoroughly mixed by shaking the tube of fluorescent reagent for approximately 10 minutes.

Thereafter, tne surface is again washed in a buffer solution comprising phosphate buffered saline at a pH of 7.7 ± 0.1 including a 0.1% sodium adize preservative. The support surface is thoroughly washed with the solution by shaking for 25 minutes. Thereafter, it is read in a fluorometer.

A serum sample without any predilution is treated in an identical manner except monospecific fluorescein isothiocyanate labelled goat antibodies to human IgA and human IgM are used in determining the concentrations of human IgA and human IgM, respectively.

The fluorescence of the foregoing samples is then compared against reference samples containing known quantities of the antigen, i.e., the immunoglobulin to be quantitated. The base reference samples are prepared from pooled human serum standardized by reference to WHO immunoglobulin reference preparations. Suitable concentrations to form a calibration curve may be found from the following chart:

| Calibrator | Typical Concentration for Three Calibrator Samples | | |
|---|---|---|---|
| | IgG | IgA | IgM |
| Low | 50 mg/dl (6.22 IU/ml) | 50 mg/dl (35.2 IU/ml) | 25 mg/dl (29.5 IU/ml) |
| Medium | 130 mg/dl (16.2 IU/ml) | 200 mg/dl (141 IU/ml) | 150 mg/dl (177 IU/ml) |
| High | 200 mg/dl (24.9 IU/ml) | 300 mg/dl (211 IU/ml) | 300 mg/dl (354 IU/ml) |

What is claimed is:
1. In a method for quantitation of antigens or antibodies in a liquid sample, the steps of
 a. sorbing said sample antibody or antigen directly onto an immunologically unreactive solid support surface sorptive for said sample antibody or antigen,
 b. exposing the sorbed surface to an aqueous reagent including an excess of labelled specific antibody or antigen immunologically reactive with said sample antigen or antibody to cause said immunological reaction to occur on said surface,
 c. removing the unreacted reagent from said surface, and
 d. measuring the quantity of reacted labelled antigen or antibody on said surface.

2. The method of claim 1 in which said sample is physically adsorbed upon said support surface.

3. The method of claim 1 in which said support surface comprises ion exchange resin and said sample is ionically bound to said resin.

4. The method of claim 1 in which the labelled portion of said labelled antibody or antigen is selected from the group consisting of a luminescent substance, a radioactive substance, an enzyme or metal containing substance.

5. The method of claim 1 in which the labelled portion of said labelled antibody or antigen comprises a fluorogen.

6. The method of claim 5 in which said reaction support surface is read fluorometrically in a window framed by opaque material.

7. The method of claim 1 in which said sample includes significant quantities of protein other than the antigen or antibody to be quantitated, said method including the step of adding to said sample prior to step (a) a predetermined quantity of buffer protein unreactive with said labelled antigen or antibody at a concentration in excess of the antigen or antibody concentration of said sample to minimize the dependence of sorbed antibody or antigen to be quantitated upon variations in the content of said other protein in said sample.

8. The method of claim 3 in which the ratio of said buffer protein to total protein of said sample is in excess of 1:1 by weight.

9. The method of claim 1 in which said support surface is selected from the group consisting of a polymeric substrate, silica gel, silicone wafers, glass, insoluble proteins, and a metallic surface.

10. The method of claim 1 in which said sample antigen or antibody or step (a) comprises antigen and said labelled antibody or antigen comprises labelled antibody.

* * * * *